United States Patent [19]
Ribier et al.

[11] Patent Number: 5,658,575
[45] Date of Patent: Aug. 19, 1997

[54] COSMETIC OR DERMATOLOGICAL COMPOSITION COMPRISING AN OIL-IN-WATER EMULSION BASED ON OILY GLOBULES PROVIDED WITH A LAMELLAR LIQUID CRYSTAL COATING

[75] Inventors: Alain Ribier; Jean-Thierry Simonnet, both of Paris; Jacqueline Griat, Ablon, all of France

[73] Assignee: L'Oreal, Paris, France

[21] Appl. No.: 301,571

[22] Filed: Sep. 7, 1994

[30] Foreign Application Priority Data

Sep. 7, 1993 [FR] France .................................. 93 10588

[51] Int. Cl.$^6$ ...................................................... A61K 7/00
[52] U.S. Cl. ........................ 424/401; 514/937; 514/938
[58] Field of Search ................................ 424/401, 490, 424/498, 502; 514/937, 938

[56] References Cited

U.S. PATENT DOCUMENTS

| | | | |
|---|---|---|---|
| 3,957,971 | 5/1976 | Oleniacz | 424/450 |
| 4,115,313 | 9/1978 | Lyon et al. | 252/309 |
| 4,811,791 | 3/1989 | Harnoy et al. | 166/305.1 |
| 4,869,842 | 9/1989 | Denis et al. | 252/121 |
| 5,152,923 | 10/1992 | Weder et al. | 252/312 |
| 5,264,586 | 11/1993 | Nicolaou et al. | 548/406 |
| 5,405,615 | 4/1995 | Mathur | 424/450 |
| 5,429,820 | 7/1995 | Kamitani et al. | 424/401 |
| 5,576,016 | 11/1996 | Amselem et al. | 424/450 |

OTHER PUBLICATIONS

Driller, H., et al., "Improved Action with Nanoemulsions", Seifen Oele Fette Wachse, vol. 121, No. 14, pp. 1025–1029, Abstract Only (1995).

Gareiss, J., et al., "Phospholipids, Liposomes, Nanoemulsions. Part 2. Effects on the Skin and Product Safety", Parfuemerie und Kosmetik, vol. 76, Mar. 1995, pp. 144, 146, 152–155, Abstract Only.

Shinoda, Kozo, et al. Emulsions and Solubilization. New York: Wiley–Interscience. 1986, pp. v to vi, 55 to 93, 159 to 169, especially 159–169.

Kirk–Othmer Encyclopedia of Chemical Technology, Third Edition, vol. 14, Entry on "Lecithin", pp. 250–269.

CA: vol. 120(8) 86055c for "Monolayer Phospholipid liposomes: Stable nanoemulsions for the Release of Lipid–Soluble Components".

Sjostrom, Brita, et al., "Structures of Nanoparticles Prepared From Oil–in–Water Emulsions", Pharmaceutical Research, vol. 12, No. 1, Issued 1995, pp. 39–48.

*Primary Examiner*—John C. Bleutge
*Assistant Examiner*—Robert H. Harrison
*Attorney, Agent, or Firm*—Oblon, Spivak, McClelland, Maier & Neustadt, P.C.

[57] ABSTRACT

Cosmetic or dermatological compositions comprising an oil-in-water type emulsion containing oily globules which are coated with a lamellar liquid crystal coating and are dispersed in an aqueous phase, in which each oily globule contains at least one lipophilic compound which is cosmetically or dermatologically active and is individually coated with a monolamellar or oligolamellar layer of at least one lipophilic surface-active agent, at least one hydrophilic surface-active agent, and at least one fatty acid, the coated oily globules having a mean diameter of less than 500 nanometers, preferably less than 200 nanometers, and the oily phase contains a basic agent in the dissolved state, exhibit good skin and hair penetration.

30 Claims, 1 Drawing Sheet

COSMETIC OR DERMATOLOGICAL COMPOSITION COMPRISING AN OIL-IN-WATER EMULSION BASED ON OILY GLOBULES PROVIDED WITH A LAMELLAR LIQUID CRYSTAL COATING

BACKGROUND OF THE INVENTION

1. Field of the Invention

The present invention relates to a cosmetic or dermatological composition comprising an oil-in-water type emulsion. It more particularly relates to a composition comprising an oil-in-water emulsion comprising oily globules which are coated with a lamellar liquid crystal coating and are dispersed in an aqueous phase. The present invention also relates to a process for the preparation of such compositions and the treatment of skin and keratinous matter by applying such compositions to skin or hair.

2. Discussion of the Background

Numerous lipophilic active compounds have an important role to play within the field of skin care. Examples of such active agents which may be mentioned are the lipophilic vitamins A, E or F, the essential oils, sunscreen agents, long-chain alkyl esters of α-hydroxy acids, anti-inflammatory agents and agents stimulating the biosynthesis of lipids and/or of proteins.

Their use is very widespread but their effectiveness is limited by their lipophilic nature. They are, in fact, only partially absorbed by the skin and diffuse only with great difficulty into the stem cells of the stratum corneum, at which cells their further penetration is stopped by the presence of aqueous compartments in the intercorneocytic spaces.

The introduction of such lipophilic active compounds into oil-in-water emulsions stabilized by a monolayer of surfactants hardly improves this state of affairs, given that these emulsions are broken as soon as they are applied to the skin, releasing at the surface of the skin an oily phase containing the lipophilic active agents which are very poorly absorbed for the reasons stated above.

Attempts to improve this state of affairs have been proposed in the prior art.

In JSCC, vol. 35, pp. 45–57 (January, February 1984), Junginger et al describe oil-in-water emulsions whose stabilization is provided by a lamellar liquid crystal three-dimensional network.

In "Secondary droplet emulsion: Contribution of liquid crystal formation to physicochemical properties and skin moisturizing effect of cosmetic emulsion" (12th International Congress IFSSC, Paris September 1992, Abstracts, Vol. I, 117–136), Suzuki et al describe these oil-in-water emulsions as forming superstructures ("secondary droplets"), aggregates of oily droplets coated with liquid crystal lamellae. These authors show that the existence of these superstructures is dependent on the presence of a fatty alcohol.

The main qualities of this type of emulsion are the stability with respect to the release of oil and a skin moisturizing effect. However, it also has its disadvantages. It is, in fact, necessary to use large amounts of surfactant in order to achieve the three-dimensional network, thereby increasing the risk of intolerance on the part of the user, which is reflected in a long "soaping" (persistence of a white color) during the application of such compositions to the skin. In addition, the oil dispersion is coarse and heterogeneous, and the oil is more sequestered by the three-dimensional network than genuinely dispersed in the form of individualized oil microdroplets. The oil droplets generated by this type of emulsion have a mean size which is very much greater than the intercorneocytic spaces that they have to cross and very much greater then the hair pores into which they have to be taken up, which contributes towards explaining the very partial penetration into skin and hair of the fatty phase and of the active agents which are dissolved therein.

Also known is the article by Dahms in *Cosmetics and Toiletries*, Vol. 101, November 1986, which describes emulsions having the same characteristics and, thus, the same drawbacks.

Thus, the need still remains for emulsions allowing an improved penetration of cosmetic or dermatological compositions into the skin and hair.

SUMMARY OF THE INVENTION

Accordingly, it is one object of the present invention to provide novel cosmetic and dermatological compositions which exhibit an improved penetration into the skin.

It is another object of the present invention to provide novel cosmetic and dermatological compositions which exhibit an improved penetration into the hair.

It is another object of the present invention to provide novel methods for preparing such compositions.

It is another object of the present invention to provide a method of treating skin by applying such a composition to skin.

It is another object of the present invention to provide a method of treating hair by applying such a composition to hair.

These and other objects, which will become apparent during the following detailed description, have been achieved by the inventors' discovery that cosmetic or dermatological compositions comprising an oil-in-water type emulsion comprising oily globules which are each coated with a lamellar liquid crystal coating and are dispersed in an aqueous phase, in which each oily globule contains at least one lipophilic compound which is cosmetically or dermatologically active and is individually coated with a monolamellar or oligolamellar layer of at least one lipophilic surface-active agent, at least one hydrophilic surface-active agent, and at least one fatty acid, the coated oily globules having a mean diameter of less than 500 nanometers, and the aqueous phase comprises a basic agent in the dissolved state, exhibit good skin and hair penetration.

The present invention also provides oil-in-water emulsions which comprise oily globules each coated with a coating of lamellar liquid crystal and dispersed in an aqueous phase, wherein each oily globule is individually coated with a monolamellar or oligolamellar layer of at least one lipophilic surface-active agent, at least one hydrophilic surface-active agent, and at least one fatty acid, the coated globules have a mean diameter of less than 500 nanometers and the aqueous phase comprises a basic agent in a dissolved state.

BRIEF DESCRIPTION OF THE DRAWING

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE PREFERRED EMBODIMENTS

Figure 1:
FIG. 1 is a micrograph of one embodiment of the present invention.

In the context of the present invention, the term lipophilic active compound is understood to refer to the active compound per se when it is itself an oil or alternatively, if it is not, the active compound dissolved in an oil. Oils which may be used are oils conventionally used as vehicles in cosmetic compositions, such as for example short-chain fatty acid triglycerides, silicone oils and the like.

The present invention provides emulsions having fatty phase droplets of extremely small size which are coated with an extremely fine mono- or oligolamellar layer. The term oligolamellar layer is understood to refer to a layer comprising from 2 to 5 lipid lamellae. Since the mean size of the coated oily globules is less than 500 nanometers and preferably less than 200 nanometers, their penetration into the intercorneocytic spaces, which are of comparable size, is greatly facilitated. Preferably, the oily globules have a polydispersity index of less than 0.1, as measured by a laser granulometer.

The active agent contained in or constituted by the oily globule may consequently be transported and delivered to the skin or hair at the site where its action will be the most effective.

According to a preferred embodiment of the invention, the lipophilic surface-active agent, the hydrophilic surface-active agent and the fatty acid each contain at least one saturated fatty chain having more than about 12 carbon atoms approximately. Even more preferably, this fatty chain contains from 16 to 22 carbon atoms.

According to another preferred embodiment of the invention, the lipophilic surface-active agent has an HLB value of between about 2 and about 5. As is well known, HLB (Hydrophilic-Lipophilic Balance) is understood to refer to the equilibrium between the size and force of the hydrophilic group and the size and force of the lipophilic group of the surface-active agent.

Examples of such lipophilic surface-active agents are sucrose distearate, diglyceryl distearate, tetraglyceryl tristearate, decaglyceryl decastearate, diglyceryl monostearate, hexaglyceryl tristearate, decaglyceryl pentastearate, sorbitan monostearate, sorbitan tristearate, diethylene glycol monostearate, the ester of glycerol and palmitic and stearic acids, polyoxyethylenated monostearate 2 EO (containing 2 oxyethylene units), glyceryl mono- and dibehenate and pentaerythritol tetrastearate.

The hydrophilic surface-active agent preferably has an HLB value of between about 8 and about 12.

The following compounds may be mentioned as examples of such hydrophilic surfactants: polyoxyethylenated sorbitan monostearate 4 EO, polyoxyethylenated sorbitan tristearate 20 EO, polyoxyethylenated monostearate 8 EO, hexaglyceryl monostearate, polyoxyethylenated monostearate 10 EO and polyoxyethylenated distearate 12 EO, and polyoxyethylenated methylglucose distearate 20 EO.

As has been stated above, the saturated fatty acid used in the context of the present invention is preferably a saturated fatty acid having from 16 to 22 carbon atoms. It is thus preferred to use palmitic acid, stearic acid, arachidic acid and behenic acid.

The coating according to the invention of the oily globules preferably requires the use of a total amount of hydrophilic surface-active agent, lipophilic surface-active agent, and fatty acid between approximately 2% and approximately 6% by weight based on the total weight of the composition. Even more preferably, this amount is between 3% and 4%. The relative amounts of lipophilic surfactant, hydrophilic surfactant, and fatty acid preferably vary within the following respective ranges: 35–55%/25–40%/15–35% by weight based on the total weight of lipophilic surfactant, hydrophilic surfactant, and fatty acid.

The fatty phase, that is to say the coated oily droplets, preferably represents 5 to 50% by weight based on the total weight of the composition. Even more preferably, this percentage is between 10 and 40. Preferably, the oil/water weight ratio is less than or equal to 1.

The weight ratio of the oily globules to the elements constituting the coating (lipophilic surfactant, hydrophilic surfactant, and fatty acid) is preferably from 2 to 13; even more preferably, this ratio is approximately equal to 7.

The basic agent contained in the aqueous phase of the compositions according to the present invention is intended to neutralize the fatty acid present in the oily phase. It must thus be present in an amount at least equal to that required to neutralize all of the fatty acid. Greater amounts of the basic agent are permissable so long as the good effects of the invention are not adversely affected.

Sodium hydroxide, triethanolamine, lysine, or alternatively arginine may, for example, be used as the basic agent.

When the compositions according to the present invention are used for the cosmetic treatment of the skin or for dermatological purposes, the active agent contained in the oily phase is, for example, chosen from antioxidants, free radical scavengers, moisturizing agents, melanoregulators, tanning accelerators, depigmenting agents, skin-coloring agents, liporegulators, thinning agents, anti-acne agents, antiseborrhoeic agents, anti-ageing agents, anti-wrinkle agents, anti-UV agents, keratolytic agents, anti-inflammatory agents, refreshing agents, cicatrizing agents, vascular protectors, antibacterial agents, antifungal agents, antiperspirants, deodorants, skin conditioners, immunomodulators, nutrients and essential oils and perfumes.

When the compositions according to the invention are used for the cosmetic treatment of keratinous matter, the active agent contained in the oily phase is, for example, chosen from melanoregulators, liporegulators, antiseborrhoeic agents, anti-ageing agents, anti-UV agents, keratolytic agents, antibacterial agents, antifungal agents, antidandruff agents, agents for combating hair loss, hair dyes, hair bleaches, reducing agents for permanent waves, hair conditioners and nutrients.

The following compounds may be mentioned as examples of active lipophiles for the treatment of the skin and/or hair, which may be used within the context of the present invention:

D-α-tocopherol, DL-α-tocopherol, D-α-tocopherol acetate, DL-α-tocopheral acetate, ascorbyl palmitate, glycerides of vitamin F, vitamin D, vitamin $D_2$, vitamin $D_3$, retinol, retinol esters (retinol palmitate, retinol propionate), β-carotene, D-panthenol, farnesol, farnesyl acetate, oils of jojoba and of blackcurrant rich in essential fatty acids, 5-n-octanoylsalicylic acid, salicylic acid, alkyl esters of α-hydroxy acids such as citric acid, lactic acid, glycolic acid, asiatic acid and madecassic acid, asiaticoside, whole extract of *Centella asiatica*, β-glycyrrhetinic acid, α-bisabolol, ceramides such as 2-oleoylamino-1,3-octadecane, phytanetriol, sphingomyelin from milk, phospholipids of marine origin which are rich in polyunsaturated essential acids, ethoxyquine, extract of romarin, extract of balm, quercetin, extract of dried microalgae (algoxan red from Algatec), essential oil of bergamot, octyl methoxycinnamate (Parsol MCX—Givaudan-Roure), butylmethoxydibenzoyl-methane (Parsol 1789—Givaudan-Roure), octyl triazone (Uvinul T150—BASF), yellow, brown, black and red iron oxides, titanium oxides which may be provided in micrometric or manometric form or in coated (perfluoroalkyl) form, 3,5-di-tert-butyl-4-hydroxybenzylidene-3-camphor, 2-benzotriazole-2-yl-4-methyl-6-[3-[1,3,3,3-tetramethyl-1-[(trimethylsilyl)oxy]-disiloxanyl]-2-methyl-propyl]phenol, perfluoronated oil (perfluorodecalin, perfluorooctyl bromide), and hyperoxygenated corn oil (Epaline 100, available from Carilene).

The compositions according to the present invention may additionally contain, in the aqueous phase, one or more free or encapsulated, cosmetically or dermatologically active hydrophilic compounds.

It is possible to use hydrophilic active agents which are conventionally used, such as antioxidants, free radical scavengers, moisturizing agents, melanoregulators, tanning accelerators, depigmenting agents, skin-coloring agents, liporegulators, thinning agents, anti-ache agents, antiseborrhoeic agents, anti-ageing agents, anti-wrinkle agents, anti-UV agents (benzene-1,4-[di(3-methylidenecamphol-10-sulfonic acid]), keratolytic agents, anti-inflammatory agents, refreshing agents, cicatrizing agents, vascular protectors, antibacterial agents, antifungal agents, antiperspirants, deodorants, skin and hair conditioners, immunomodulators, nutrients, anti-dandruff agents, agents for combating hair loss, hair dyes, hair bleaches, reducing agents for permanent waves and essential oils and perfumes.

When it is provided in the encapsulated state, this compound may be incorporated into a lipid vesicle obtained from ionic or nonionic lipids or from a mixture of the two. It may also be incorporated into lipid nanoparticles such as nanospheres, nanosponges or nanocapsules.

The incorporation of lipid vesicles into the compositions of the invention is particularly advantageous because of the complementary nature and the good compatibility of these two types of vehicles, namely, on the one hand, oily globules containing lipophilic active agents, with a preferred mean size in the region of 200 nm which are delimited by their lamellar liquid crystal coating, and, on the other hand, lipid vesicles having an aqueous core containing hydrophilic active agents, with a preferred mean size in the region of 200 nm, which are delimited by their lamellar wall.

The inventors have furthermore observed that the lipid vesicles based on unsaturated natural ionic lipids, which are particularly sensitive to the presence of surfactants in the aqueous phase (which is the case in the standard emulsions) and to the presence of peroxides, were conserved particularly well in the compositions of the invention based on surfactants containing saturated fatty chains having more than 12 carbon atoms.

The compositions of the invention may also contain, in the aqueous phase, various complementary additives such as preserving agents, sequestering agents, gelling agents and the like.

The compositions of the invention may also contain, in the fatty phase, various complementary additives such as oils, waxes or gums having, for example, emollient or lubricating properties.

The compositions are most often provided in milk, cream or gel form, other modes of presentation not being excluded.

In another embodiment, the present invention provides a process for the preparation of the compositions described above, comprising:

(i) mixing (a) a fatty phase, comprising the lipophilic surfactant, the hydrophilic surfactant, the fatty acid and the cosmetically or dermatologically active compound and (b) an aqueous phase comprising the basic agent by stirring to obtain a mixture; and (ii) homogenizing the mixture by subjecting the mixture to cavitation.

In the first step, the mixture is subjected to conventional stirring, for example in a homogenizer rotating at a rate approximately between 500 and 5000 rev/min for a time approximately between 10 and 60 minutes and at a temperature approximately between 20° and 95° C.

The homogenization based on the principle of cavitation in the second step is a key step of the process according to the invention. This homogenization results from the cavitation phenomenon created and maintained within the mixture, which mixture is then in liquid form, by movement at a linear velocity of at least 100 m/s.

The homogenizing may be performed by using a high pressure homogenizer operating at pressures approximately between 200 and 1000 bar. The principle of the use of this type of homogenizer is well known to those skilled in the art. The process is performed by successive passages, generally from 2 to 10 passages, at the selected pressure, the mixture being returned to normal pressure between each passage.

The homogenizing of the second step may also be carried out under the action of ultrasound or alternatively by the use of a homogenizer equipped with a rotor-stator type head.

When the aqueous phase contains hydrophilic active agents which are cosmetically or dermatologically active, if the latter are introduced in the free state they may be introduced in the mixing step (i). If, on the contrary, they are introduced in the encapsulated state, they must be introduced in a subsequent third step. In this case, they are introduced by simple mixing.

Other features of the invention will become apparent in the course of the following descriptions of exemplary embodiments which are given for illustration of the invention and are not intended to be limiting thereof.

EXAMPLES

In the following examples, all percentages are given in terms of percent by weight based on the total weight of the composition unless otherwise specified.

In these examples, the process is performed using the following procedure:

The oily phase A1 and the aqueous phase B are heated separately to a temperature of 80° C.

Phase B is poured onto phase A, with stirring of 4000 rev/min provided by a Moritz homogenizer of type Turbo Lab 2100, and these stirring and temperature conditions are maintained for 30 minutes.

The mixture is then introduced into a Soavi high pressure homogenizer of type OBL, which is adjusted to a pressure of 500 bar, for 3 successive passages.

A stabilized oil-in-water emulsion is thus obtained, the oily globules of which have a mean size of less than 200 nm and a polydispersity index of less than 0.1, as measured by a laser granulometer of type AMTECH BI 90.

The emulsion is subsequently cooled to bring it back to room temperature, which takes approximately 60 minutes. The oil phase A2 is then added to the emulsion and the whole mixture is subjected to the stirring given by the Turbo Lab 2100 at a rate of 3000 rev/min for 10 min, after which this premixture is introduced into the Soavi-OBL, which is adjusted to a pressure of 350 bar, for a further two passages.

After each of these two passages, the product is recooled to room temperature.

The phase C is added to this emulsion A1+B+A2, and the whole mixture is stirred using a Rayneri homogenizer equipped with a turbine of deflocculent type, at a rate of 2500 rev/min for 30 min at room temperature.

Example 1

Facial day cream intended for dry skin.

| Phase A1: | |
|---|---|
| Sucrose distearate marketed by the company "STEARINERIE DUBOIS" | 2% |
| Oxyethylenated sorbitan stearate containing 4 mol of ethylene oxide, marketed under the name "TWEEN 61" by the company ICI | 1.4% |
| Stearic acid | 0.75% |
| Stearyl heptanoate marketed by the company DRAGOCO under the name PCL solid | 5.50% |
| Vaseline codex | 2.10% |
| Avocado oil | 4.50% |
| Jojoba oil | 4.10% |
| Volatile silicone oil | 3.70% |
| Vitamin E acetate | 0.50% |
| D-α-Tocopherol marketed by the company HENKEL under the name "COPHEROL 1300" | 0.30% |
| Phase A2: | |
| Silicone gum marketed by the company DOW CORNING under the name "Q$_2$-1403 Fluid" | 4.00% |
| Perfume | 0.3% |
| Propylparaben | 0.1% |
| Phase B: | |
| Glycerine | 5.00% |
| Methylparaben | 0.3% |
| Triethanolamine | 0.40% |
| Demineralized water qs | 100% |
| Phase C: | |
| Mixture of carboxyvinyl polymers marketed under the name "CARBOPOL 940" by the company GOODRICH | 0.30% |
| Demineralized water | 9.70% |

The mean size of the oil globules of the stabilized emulsion is 170 nm with a polydispersity index of 0.09.

A smooth and shiny white cream is thus obtained which, on application, is found to be very soft and non-greasy. After applying for several days, an improvement in the state of dryness of the facial skin is observed.

Example 2

Facial anti-ageing day cream.

| Phase A1: | |
|---|---|
| Sucrose distearate marketed by the company "STEARINERIE DUBOIS" | 1.75% |
| Oxyethylenated sorbitan stearate containing 4 mol of ethylene oxide, marketed under the name "TWEEN 61" by the company ICI | 1.15% |
| Stearic acid | 0.75% |
| Stearyl heptanoate | 4.00% |
| Vaseline codex | 1.50% |
| Avocado oil | 3.20% |
| Jojoba oil | 3.00% |
| Volatile silicone oil | 2.70% |
| Vitamin E acetate | 1.00% |
| Natural D-a-tocopherol marketed by the company HENKEL under the name "COPHEROL 1300", | 1.00% |
| Vitamin F glycerides | 3.00% |
| Retinol palmitate marketed by FLUKA, assayed at 1500 IU/mg | 0.5% |
| Phase A2: | |
| Silicone gum marketed by the company DOW CORNING under the name "Q$_2$-1403 Fluid" | 3.00% |
| Propylparaben | 0.2% |
| Perfume | 0.3% |
| Phase B: | |
| Glycerine | 3.00% |
| Hydroxyproline | 1.00% |
| D-Panthenol | 1.00% |
| Triethanolamine | 0.35% |
| Methylparaben | 0.3% |
| Demineralized water qs | 100% |
| Phase C: | |
| Mixture of carboxyvinyl polymers marketed under the name "CARBOPOL 940" by the company GOODRICH | 0.40% |
| Demineralized water | 9.60% |

The mean size of the oil globules of the stabilized emulsion is 190 nm with a polydispersity index of 0.07.

A smooth, white cream is obtained, which feels fresh, supple and very comfortable on application.

Example 3

Body moisturizing milk.

| Phase A1: | |
|---|---|
| Sorbitan stearate marketed by the company ICI under the name "SPAN 60" | 1.5% |
| Oxyethylenated sorbitan stearate containing 4 mol of ethylene oxide, marketed under the name "TWEEN 61" by the company ICI | 1% |
| Stearic acid | 0.5% |
| Behenic acid | 0.25% |
| Stearyl heptanoate | 3.00% |
| Vaseline codex | 1.00% |
| Volatile silicone oil | 4.00% |
| Jojoba oil | 2.00% |
| Vitamin E acetate | 0.50% |
| Phase A2: | |
| Silicone gum marketed by the company DOW CORNING under the name "Q2-1403 Fluid" | 2.00% |
| Propylparaben | 0.1% |
| Perfume | 0.3% |
| Phase B: | |
| Glycerine | 5.00% |
| Methylparaben | 0.30% |
| Propylene glycol | 3.00% |
| Triethanolamine | 0.25% |
| Demineralized water qs | 100% |
| Phase C: | |
| Mixture of carboxyvinyl polymers marketed under the name "CARBOPOL 940" by the company GOODRICH | 0.20% |
| Demineralized water | 9.80% |

The mean size of the oil globules of the stabilized emulsion is 165 nm with a polydispersity index of 0.09.

A fluid milk is obtained which feels fresh and gives very good covering.

Example 4

Night cream containing nonionic liposomes for stressed and wrinkled skin.

| Phase A1: | |
|---|---|
| Tetraglyceryl tristearate marketed by the company NIKKOL under the name "TETRAGLYN 3 S" | 2% |
| Oxyethylenated sorbitan stearate containing 4 mol of ethylene oxide, marketed under the name "TWEEN 61" by the company ICI | 1.4% |
| Stearic acid | 1.0% |
| Stearyl heptanoate | 5.50% |
| Vaseline codex | 2.10% |
| Macadamia oil | 4.5% |
| Apricot almond oil | 3.50% |
| Volatile silicone oil | 3.70% |
| Vitamin E acetate | 1.00% |
| Vitamin F glycerides | 3.00% |
| Natural D-α-Tocopherol marketed by the company HENKEL under the name "COPHEROL 1300" | 0.50% |
| Phase A2: | |
| Silicone gum marketed by DOW CORNING under the name "$Q_2$-1403" | 4.00% |
| Propylparaben | 0.1% |
| Perfume | 0.3* |
| Phase B: | |
| Methylparaben | 0.3% |
| Triethanolamine | 0.4% |
| Demineralized water qs | 100% |
| Phase C: | |
| This is broken down here into two phases, C1 and C2 | |
| Phase C1: Vesicle phase | |
| Tetraglyceryl stearate marketed by NIKKOL under the name "TETRAGLYN 3 S" | 0.46% |
| Cholesterol | 0.46% |
| N-Stearoylglutamic acid monosodium salt marketed under the name "ACYLGLUTAMATE HS 11" by the company AJINOMOTO | 0.08% |
| Glycerine | 3.00% |
| Hydroxyproline | 1.00% |
| Demineralized water | 5.00% |

This phase is prepared in the following way:

The 3 lipids constituting the lipid wall of the vesicles are heated to the temperature of 115° C. which is necessary and sufficient to achieve the co-fusion thereof. A transparent liquid mixture is thus obtained, which is cooled to a temperature of 90° C.

The remainder of the aqueous phase C1 is then added in order to perform the hydration of the lipid mixture at this same temperature of 90° C. by slow stirring for 60 minutes. This mixture is cooled to 60° C. and is then introduced into the Soavi homogenizer of type OBL, which is adjusted to a pressure of 500 bar, for 3 successive passages.

| Phase C2: | |
|---|---|
| Mixture of carboxyvinyl polymers marketed under the name "CARBOPOL 940" by the company GOODRICH | 0.3% |
| Demineralized water | 9.70% |

Phase C1, cooled to room temperature, is mixed with the gelified phase C2 in order to constitute the phase C.

The mean size of the oil globules of the stabilized emulsion is 180 nm and the polydispersity index is 0.07.

A smooth and shiny white cream which feels very comfortable after application is obtained.

Example 5

Day cream containing liposomes, for sensitive, stressed and wrinkled skin.

| Phase A1: | |
|---|---|
| Diglyceryl monostearate marketed by the company NIKKOL under the reference "DGMS" | 1.50% |
| Polyoxyethylenated monostearate 8-EO marketed by ICI under the name Myrj 45 | 1.00% |
| Stearic acid | 0.75% |
| Stearyl heptanoate | 4.00% |
| Vaseline codex | 1.00% |
| Volatile silicone | 3.20% |
| Jojoba oil | 3.00% |
| Sweet almond oil | 2.70% |
| Vitamin E acetate | 0.50% |
| Natural D-α-tocopherol marketed by the company HENKEL under the name "COPHEROL 1300", | 1.00% |
| Octyl methoxycinnamate marketed by the company GIVAUDAN under the name "PARSOL MCX" | 2.00% |
| Butylmethoxydibenzoylmethane marketed by the company GIVAUDAN under the name "PARSOL 1789" | 0.5% |
| Phase A2: | |
| Silicone gum marketed by the company DOW CORNING under the name "$Q_2$-1403 Fluid" | 3.00% |
| Preservative | 0.1% |
| Perfume | 0.3% |
| Phase B: | |
| Preservatives | 0.1% |
| Perfume | 0.3% |
| Triethanolamine | 0.35% |
| Demineralized water qs | 100% |
| Phase C: | |
| This is composed of two phases, C1 and C2: | |
| Phase C1: Vesicle phase | |
| Mixture of phospholipids in a water/alcohol mixture marketed under the name "NATIPIDE II" by the company NATTERMAN PHOSPHOLIPID | 5% |
| Glycerine | 3% |
| Demineralized water | 9% |
| Hydroxyproline | 1% |

This phase is prepared by dispersing NATIPIDE II in the remainder of the aqueous phase, at room temperature, using a magnetic stirring bar rotating at a rate of 300 rev/min for 30 min.

| Phase C2: | |
|---|---|
| Carboxyvinyl polymer marketed by the company SIGMA under the name "SYNTHALEN K" | 0.5% |
| Demineralized water | 9.5% |

Phase C1 is then mixed with phase C2 in order to constitute phase C.

The mean size of the oil globules of the stabilized emulsion is 180 nm and the polydispersity index is 0.08.

A smooth, white cream with a fine, non-greasy texture and a very comfortable feel is obtained.

Example 6

Restructuring night cream for rough skin.

| Phase A1: | |
|---|---|
| Diglyceryl monostearate marketed by the company NIKKOL under the reference DGMS | 2% |
| Polyoxyethylenated monostearate 10-EO marketed by NIKKOL under the name Mys 10 | 1.35% |
| Stearic acid | 1% |
| Stearyl heptanoate | 5.50% |
| Vaseline codex | 2.00% |
| Vitamin E acetate | 3.40% |
| Natural D-α-tocopherol marketed by the company HENKEL under the name "COPHEROL 1300" | 1% |
| Stabilized mixture vegetable oils marketed by the company NESTLE under the name "Huile Balance" | 3.4% |
| Mixture of farnesol and farnesyl acetate marketed by the company INDUCHEM under the name "UNIBIOVIT B 33" | 1.0% |
| Retinol palmitate from Fluka, assayed at 1500 IU/mg | 0.5% |
| Volatile silicone | 4.6% |
| 3,5-Di-tert-butyl-4-hydroxybenzylidene-3-camphor marketed by the company CHIMEX under the name "MEXORYL SAD" | 0.5% |
| Phase A2: | |
| Silicone gum marketed by the company DOW CORNING under the name "$Q_2$-1403 Fluid" | 6% |
| Phase B: | |
| Preservatives | 0.4% |
| Triethanolamine | 0.4% |
| Glycerine | 3.0% |
| Hydroxyproline | 1.0% |
| D-Panthenol | 1.0% |
| Demineralized water qs | 100% |
| Phase C: | |
| Mixture of carboxyvinyl polymers marketed by the company GOODRICH under the name "CARBOPOL 940" | 0.30% |
| Demineralized water | 9.70% |

The mean size of the oil globules of the stabilized emulsion is 180 nm with a polydispersity index of 0.07.

A thick, white cream which feels rich but non-greasy and very comfortable on application is obtained.

In addition to the count performed using the AMTECH BI 90 laser diffusion granulometer, which allows the volume-distribution mean size of the coated oily globules to be determined, equivalent to 180 nm with a polydispersity index of 0.07, this cream is subjected to electron microscopy examination by cryofracture. It may thus be observed in the characteristic micrograph given in FIG. 1 (magnification× 40,000; scale 1 mm (on the photograph)=25 nm (object photographed)), that the oily globules are individual, independent from each other, coated with a predominantly unilamellar, sometimes oligolamellar, layer and that the mean size of most of the coated oily globules is approximately 100 nm.

Example 7

High-protection sun cream.

| Phase A1: | |
|---|---|
| Sucrose distearate marketed by the company STEARINERIE DUBOIS | 2% |
| Oxyethylenated sorbitan stearate containing 4 mol of ethylene oxide, marketed by the company ICI under the name "TWEEN 61" | 1.35% |
| Stearic acid | 1% |
| Vaseline codex | 2.10% |
| Liquid purcellin | 5.50% |
| Octyl methoxycinnamate marketed by the company GIVAUDAN ROURE under the name "Parsol MCX" | 7% |
| Butyl methoxydibenzoylmethane marketed by the company GIVAUDAN ROURE under the name "Parsol 1789" | 4% |
| Volatile silicone | 3% |
| Jojoba oil | 4% |
| Vitamin E acetate | 0.5% |
| Phase A2: | |
| Silicone gum marketed by the company DOW CORNING under the name "$Q_2$-1403 Fluid" | 4.00% |
| Preservatives | 0.1% |
| Phase B: | |
| Preservatives | 0.3% |
| Disodium EDTA | 0.05% |
| Glycerine | 3% |
| Triethanolamine | 0.4% |
| Demineralized water qs | 100% |
| Phase C: | |
| Carboxyvinyl polymer marketed by the company SIGMA under the name "SYNTHALEN K" | 0.4% |
| Demineralized water | 9.6% |

The average size of the oil globules of the stabilized emulsion is 160 nm with a polydispersity index of 0.07.

A thick, white cream is thus obtained, which has a protection factor of SPF 11 and which is of good remanence on washing with water and has a good persistence with time.

Example 8

Perfumed body milk.

| Phase A: | |
|---|---|
| Diglyceryl monostearate marketed by the company NIKKOL under the name DGMS | 1.5% |
| Oxyethylenated sorbitan stearate containing 4 mol of ethylene oxide, marketed by the company ICI under the name "TWEEN 61" | 1% |
| Stearic acid | 0.75% |
| Stearyl heptanoate | 2% |
| Sesame oil | 6% |
| Volatile silicone oil | 2% |
| Essential oil of bergamot (Bergaptene-free) | 8% |
| Phase B: | |
| Silicone gum marketed by the company DOW CORNING under the name "$Q_2$-1403 Fluid" | 2% |
| Preservative | 0.1% |

-continued

| Phase C: | |
|---|---|
| Glycerine | 3% |
| Propylene glycol | 5% |
| Preservatives | 0.3% |
| Triethanolamine | 0.3% |
| Demineralized water qs | 100% |

The average size of the oil globules of the stabilized emulsion is 160 nm with a polydispersity index of 0.06.

A very fluid, white milk is obtained which may be sprayed using a pump-bottle dispenser. Remanent perfuming properties with time.

Example 9

Day cream containing nonionic liposomes, for combination skins.

| Phase A1: | |
|---|---|
| Diglyceryl distearate marketed by the company NIHON EMULSION under the name "EMALEX DSG2" | 1.5% |
| Polyoxyethylenated methylglucose distearate 20-EO marketed by the company AMERCHOL under the name Glucam E 20 distearate | 1% |
| Stearic acid | 0.25% |
| Palmitic acid | 0.5% |
| Stearyl heptanoate | 4.00% |
| Vaseline codex | 1.50% |
| Jojoba oil | 3.00% |
| Macadamia oil | 3.20% |
| Volatile silicone oil | 3.00% |
| Vitamin E acetate | 0.50% |
| Natural D-α-tocopherol marketed by the company HENKEL under the name "COPHEROL 1300" | 0.3% |
| Vitamin F glyceride | 1% |
| Phase A2: | |
| Silicone gum marketed by the company DOW CORNING under the name "Q$_2$-1403 Fluid" | 3% |
| Preservatives | 0.1% |
| Perfume | 0.3% |
| Phase B: | |
| Propylene glycol | 3% |
| Preservatives | 0.4% |
| Triethanolamine | 0.3% |
| Demineralized water qs | 100% |
| Phase C: | |

This phase is broken down into two phases: C1 and C2.
The procedure is as in Example 4.

| Phase C1: Vesicle phase | |
|---|---|
| Sucrose monodipalmitostearate marketed by the company GRILLO under the name "GRILLOTEN PSE 141G" | 0.46% |
| Cholesterol | 0.46% |
| Glutamic acid monosodium salt marketed by the company AJINOMOTO under the name "ACYLGLUTARATE HS11" | 0.08% |
| Glycerine | 3.00% |
| Hydroxyproline | 1.00% |
| Demineralized water | 5.00% |
| Phase C2: | |
| Carboxyvinyl Polymer marketed by the company SIGMA under the name "SYNTHALEN K" | 0.3% |
| Demineralized water | 9.70% |

The average size of the oil globules in the stabilized emulsion is 180 nm with a polydispersity index of 0.07.

A fine and shiny white cream is obtained which feels very comfortable and non-greasy and is evanescent on application.

Example 10

Protective day cream for skin with dry tendency.

| Phase A: | |
|---|---|
| Sucrose distearate marketed by the company STEARINERIE DUBOIS | 1.75% |
| Oxyethylenated sorbitan stearate containing 4 mol of ethylene oxide, marketed by the company ICI under the name "TWEEN 61" | 1.15% |
| Stearic acid | 0.85% |
| pentaerythritol tetrastearate marketed by the company AKZO under the name "KESSCO PTS" | 1% |
| Mixture of glyceryl mono- and dibehenate marketed by the company GATTEFOSSE under the name "glyceryl BEHENATE WL 251" | 1% |
| Vaseline codex | 1.5% |
| Stearyl heptanoate | 5.% |
| Jojoba oil | 3.50% |
| Sweet almond oil | 3.00% |
| Volatile silicone oil | 3.00% |
| Vitamin F glyceride | 1.00% |
| Vitamin E acetate | 0.50% |
| Phytantriol marketed by the company HOFFMANN LAROCHE | 1.00% |
| Phase A2: | |
| Silicone gum marketed by the company DOW CORNING under the name "Q$_2$-1403 Fluid" | 3% |
| Preservative | 0.1% |
| Perfume | 0.3% |
| Phase B: | |
| Preservatives | 0.3% |
| Glycerine | 3.00% |
| Hydroxyproline | 1.00% |
| Lysine | 0.4% |
| Demineralized water qs | 100% |
| Phase C: | |
| Carboxyvinyl polymer marketed by the company SIGMA under the name "SYNTHALEN K" | 0.4% |
| Demineralized water | 9.6% |

The average size of the oil globules of the stabilized emulsion is 200 nm with a polydispersity index of 0.05.

A smooth, white cream is obtained which has good protecting qualities, in particular for dry skin during the winter period.

Example 11

Tinted cream intended for fair skin.

| Phase A1: | |
|---|---|
| Sucrose distearate marketed by the company STEARINERIE DUBOIS | 2% |
| Oxyethylenated sorbitan stearate containing 4 mol of ethylene oxide, marketed by the company ICI under the name "TWEEN 61" | 1.35% |
| Stearic acid | 1% |
| Stearyl heptanoate | 5.5% |
| Vaseline codex | 2.1% |

-continued

| | |
|---|---|
| Volatile silicone oil | 6.0% |
| Avocado oil | 4.0% |
| Jojoba oil | 4.0% |
| DL-α-Tocopherol acetate | 0.5% |
| Ethoxyquine | 0.03% |
| Phase A2 | |
| Silicone gum marketed by the company DOW CORNING under the name "Q2-1403 Fluid" | 4.00% |
| Propylparaben | 0.1% |
| Perfume | 0.3% |
| Phase B: | |
| Methylparaben | 0.1% |
| Germal II | 0.3% |
| Dequest 2046 | 0.05% |
| Glycerine | 3.0% |
| Triethanolamine | 0.3% |
| Demineralized water | 45.0% |
| Phase C: | |
| Saponite marketed by the company VANDERBILT under the name "VEEGUM" | 0.35% |
| Yellow iron oxides | 0.77% |
| Brown iron oxides | 0.77% |
| Black iron oxides | 0.35% |
| Titanium dioxides | 5.11% |
| Xanthan gum marketed by the company KELCO under the name "KELTROL T" | 0.20% |
| Demineralized water qs | 100% |

The average size of the coated oil globules is 180 nm with a polydispersity index of 0.08.

A smooth, tinted cream is thus obtained, which very uniformly covers the imperfections in facial color tone.

Example 12

Anti-sun day cream with a high protection factor.

| | |
|---|---|
| Phase A1: | |
| Sucrose distearate marketed by the company STEARINERIE DUBOIS | 1.5% |
| Oxyethylenated sorbitan stearate containing 4 mol of ethylene oxide, marketed by the company ICI under the name "TWEEN 61" | 1.0% |
| Stearic acid | 0.5% |
| Arachidic acid | 0.25% |
| Stearyl heptanoate | 5.5% |
| Vaseline codex | 2.1% |
| Avocado oil | 4.0% |
| Jojoba oil | 4.0% |
| DL-α-Tocopherol acetate | 0.5% |
| Octyl methoxycinnamate marketed by the company GIVAUDAN ROURE under the name "PARSOL MCX" | 2.0% |
| Butyl methoxycinnamate marketed by the company GIVAUDAN ROURE under the name "PARSOL 1789" | 0.5% |
| Ethoxyquine | 0.03% |
| Phase A2: | |
| Nanometric titanium dioxide marketed by the company TAYCA under the name "MT 100 T" | 10.0% |
| Dodecamethylcyclohexasiloxane marketed by the company HERCULES | 10.0% |
| Silicone gum marketed by the company DOW CORNING under the name "Q2-1403 Fluid" | 4.0% |
| Phase B: | |
| Preservatives | 0.4% |

-continued

| | |
|---|---|
| Sequestering agent | 0.05% |
| Glycerine | 3.0% |
| Triethanolamine | 0.4% |
| Demineralized water | 42.67% |
| Phase C: | |
| Mixture of carboxyvinyl polymers marketed by the company GOODRICH under the name "CARBOPOL 940" | 0.3% |
| Demineralized water qs | 100% |

The average size of the coated oil globules is 170 nm with a polydispersity index of 0.12.

A smooth, matt, thick (46 poises) white cream is thus obtained.

Example 13

Vitamin-containing day cream for facial skin care.

| | |
|---|---|
| Phase A1: | |
| Sucrose distearate marketed by the company STEARINERIE DUBOIS | 1.75% |
| Oxyethylenated sorbitan stearate containing 4 mol of ethylene oxide, marketed by the company ICI under the name "TWEEN 61" | 1.15% |
| Stearic acid | 0.75% |
| D-α-Tocopherol acetate | 1.0% |
| Vitamin F glycerides | 2.0% |
| Retinol palmitate assayed at 1500 IU/mg marketed by the company FLUKA | 0.5% |
| Ascorbyl palmitate | 0.5% |
| Mixture of farnesol and farnesyl acetate marketed by the company INDUCHEM under the name "UNIBIOVIT B 33" | 2% |
| Blackcurrant oil | 3% |
| Ethoxyquine | 0.03% |
| Phase B: | |
| Glycerine | 3.0% |
| Hydroxyproline | 1.0% |
| D-Panthenol | 1.0% |
| Lysine | 0.4% |
| Demineralized water | 50% |
| Phase C: | |
| Carboxyvinyl polymer marketed by the company SIGMA under the name "SYNTHALEN K" | 0.4% |
| Demineralized water qs | 100% |

A smooth, fluid, white cream is thus obtained, which has a stimulating effect on tired, lackluster skin.

Example 14

Day cream with sunscreen.

| | |
|---|---|
| Phase A1: | |
| Sucrose distearate available from STEARINERIE DUBOIS | 2% |
| Sorbitan oxyethylene stearate with 4 mol of ethylene oxide available from ICI under the name "TWEEN 61" | 1.35% |
| Stearic acid | 1% |
| Stearyl heptanoate | 5.5% |
| Vaseline codex | 2.1% |
| Propylparaben | 0.08% |
| Volatile silicone oil | 3.7% |
| Java oil | 4.5% |

-continued

| | |
|---|---|
| Avocado oil | 4.1% |
| D-tocopherol acetate | 0.3% |
| 2-benzotriazol-2-yl-4-methyl-6-[3-[1,3,3,3-tetramethyl-1-[(trimethylsilyl)-oxy]disiloxanyl]-2-methyl-propyl]phenol | 7.0% |
| Phase A2 | |
| Silicone gum available from DOW CORNING under the name of "Q2-1403 Fluid: | 3.0% |
| Phase B: | |
| Preservatives | 0.4% |
| Glycerine | 3.0% |
| Triethanolamine | 0.4% |
| Demineralized water | 51.0% |
| Phase C: | |
| Carboxyvinyl polymer mixture available from GOODRICH under the name of "CARBOPOL 940" | 0.3% |
| Demineralized water qs | 100% |

The mean size of the oily globules is 200 nm with a polydispersity factor of 0.09.

The result is a white, smooth, sparking thick cream (60 poise).

Example 15

Day cream.

| | |
|---|---|
| Phase A: | |
| Diglyceride distearate available from NIHON EMULSION under the name Emalex DSG 2 | 1.5% |
| Methyl glucose polyoxyethylene distearate 20-OE available from AMERCHOL under the name of Glucam E20 distearate | 1.0% |
| Stearic acid | 0.75% |
| Stearyl heptanoate | 2.0% |
| Perfluorodecalin available from FLUOROCHEM Limited | 6.0% |
| Sesame oil | 6.0% |
| Volatile silicone oil | 3.0% |
| Java oil | 3.5% |
| Propylparaben | 0.1% |
| Natural D-tocopherol available from HENKEL under the name "COPHEROL 1300" | 0.3% |
| Phase B: | |
| Preservatives | 0.4% |
| Glycerine | 3.0% |
| Tiethanolamine | 0.3% |
| Demineralized water qs | 60% |
| Phase C: | |
| Carboxyvinyl polymer mixture available from GOODRICH under the name of "CARBOPOL 940" | 0.3% |
| Demineralized water qs | 100% |

The result is a very fluid, fine, white and sparkling cream.

Obviously, numerous modifications and variations of the present invention are possible in light of the above teachings. It is therefore to be understood that, within the scope of the appended claims, the invention may be practiced otherwise than as specifically described herein.

What is claimed as new and desired to be secured by Letters Patent of the United States is:

1. A cosmetic or dermatological composition, comprising an oil-in-water emulsion comprising oily globules which are each coated with a lamellar liquid crystal coating and are dispersed in an aqueous phase, each oil globule comprising at least one lipophilic compound which is cosmetically or dermatologically active and is individually coated with a monolamellar or oligolamellar layer of a mixture of at least one lipophilic surface active agent, at least one hydrophilic surface-active agent, and at least one fatty acid, said coated oil globules having a mean diameter of less than 500 nanometers, and said aqueous phase comprising a basic agent in the dissolved state, wherein said lipophilic surface-active agent, said hydrophilic surface-active agent, and said fatty acid are present in a combined amount of between 2 and 6% by weight based on the total weight of said composition.

2. The composition of claim 1, wherein said oily globules have a mean diameter of less than 200 nanometers.

3. The composition of claim 1, wherein said lipophilic surface-active agent, said hydrophilic surface-active agent, and said fatty acid each contain at least one saturated fatty chain having more than about 12 carbon atoms.

4. The composition of claim 3, wherein said saturated fatty chain has from 16 to 22 carbon atoms.

5. The composition of claim 1, wherein said lipophilic surface-active agent has an HLB value of between 2 and 5.

6. The composition of claim 5, wherein said lipophilic surface-active agent having an HLB value of between 2 and 5 is selected from the group consisting of sucrose distearate, diglyceryl distearate, tetraglyceryl tristearate, decaglyceryl decastearate, diglyceryl monostearate, hexaglyceryl tristearate, decaglyceryl pentastearate, sorbitan monostearate, sorbitan tristearate, diethylene glycol monostearate, the ester of glycerol and palmitic and stearic acids, polyoxyethylenated monostearate 2 EO (containing 2 ethylene oxide units), glyceryl mono- and dibehenate, and pentaerythritol tetrastearate.

7. The composition of claim 1, wherein said hydrophilic surface-active agent has an HLB value of between 8 and 12.

8. The composition of claim 7, wherein said hydrophilic surface-active agent having an HLB value of between 8 and 12 is selected from the group consisting of polyoxyethylenated sorbitan monostearate 4 EO, polyoxyethylenated sorbitan tristearate 20 EO, polyoxyethylenated monostearate 8 EO, hexaglyceryl monostearate, polyoxyethylenated monostearate 10 EO, polyoxyethylenated distearate 12 EO, and polyoxyethylenated methylglucose distearate 20 EO.

9. The composition of claim 1, wherein said fatty acid is selected from the group consisting of palmitic acid, stearic acid, arachidic acid, and behenic acid.

10. The composition of claim 1, wherein said lipophilic surface-active agent, said hydrophilic surface active agent, and said fatty acid are present in a combined amount of between 3 and 4% by weight based on the total weight of said composition.

11. The composition of claim 1, wherein said lipophilic surface-active agent, said hydrophilic surface-active agent, and said fatty acid are present in amounts of 35–55%, 25–40% and 15–35% by weight, respectively, based on the total weight of said lipophilic surface-active agent, said hydrophilic surface-active agent, and said fatty acid.

12. The composition of claim 1, wherein said coated oily globules are present in an amount of from 5 to 50% by weight based on the total weight of said composition.

13. The composition of claim 12, wherein said coated oily globules are present in an amount of from 10 to 40% by weight based on the total weight of said composition.

14. The composition of claim 1, wherein the weight ratio of said oily globules to said surfactants comprising said coating is between 2 and 13.

15. The composition of claim 14, wherein the weight ratio of said oily globules to said surfactants comprising said coating is about 7.

16. The composition of claim 1, wherein said basic agent is dissolved in the aqueous phase in an amount at least equal to the amount required to neutralize said fatty acid.

17. The composition of claim 1, wherein said basic agent is selected from the group consisting of sodium hydroxide, triethanolamine, lysine, and arginine.

18. The composition of claim 1, wherein said aqueous phase further comprises one or more free or encapsulated, cosmetically or dermatologically active hydrophilic compounds.

19. The composition of to claim 18, wherein said cosmetically or dermatologically active hydrophilic compound is encapsulated in an ionic and/or nonionic lipid vesicle or in a nanoparticle, nanosphere, nanosponge or nanocapsule.

20. The composition of claim 1, wherein said oily globules comprise at least one fatty or lipophilic substance having a skin-care activity.

21. The composition of claim 20, wherein said fatty or lipophilic substance is selected from the group consisting of antioxidants, free radical scavengers, moisturizing agents, melanoregulators, tanning accelerators, depigmenting agents, skin-coloring agents, liporegulators, thinning agents, anti-acne agents, antiseborrhoeic agents, anti-ageing agents, anti-wrinkle agents, anti-UV agents, keratolytic agents, anti-inflammatory agents, refreshing agents, cicatrizing agents, vascular protectors, antibacterial agents, antifungal agents, antiperspirants, deodorants, skin conditioners, immunomodulators, nutrients, essential oils and perfumes.

22. The composition of claim 21, wherein said fatty or lipophilic substance is selected from the group consisting of D-α-tocopherol DL-α-tocopherol, D-α-tocopherol acetate, DL-α-tocopherol acetate, ascorbyl palmitate, glycerides of vitamin F, vitamin D, vitamin $D_2$, vitamin $D_3$, retinol, retinol esters, β-carotene, D-panthenol, farnesol, farnesyl acetate, oils of jojoba and of blackcurrant rich in essential fatty acids, 5-n-octanoylsalicylic acid, salicylic acid, alkyl esters of α-hydroxy acids, asiaticoside, whole extract of Centella asiatica, β-glycyrrhetinic acid, α-bisabolol, 2-oleoylamino-1,3-octadecane, phytanetriol, sphingomyelin from milk, phospholipids of marine origin which are rich in polyunsaturated essential acids, ethoxyquine, extract of romarin, extract of balm, quercetin, extract of dried microalgae, essential oil of bergamot, octyl methoxycinnamate, butylmethoxydibenzoylmethane, octyl triazone, yellow, brown, black and red iron oxides, titanium oxides which may be provided in micrometric or nanometric form or in coated form, 3,5-di-tert-butyl-4-hydroxybenzylidene-3-camphor, 2-benzotriazole-2yl-4-methyl-6-[3-[1,3,3,3-tetramethyl-1-[(trimethylsilyl)oxy]disiloxanyl]-2-methylpropyl]phenol, perfluoronated oil, and hyperoxygenated corn oil.

23. The composition of claim 1, wherein said oily globules comprise at least one fatty or lipophilic substance having a hair-care activity.

24. The composition of claim 23, wherein said fatty or lipophilic substance is selected from the group consisting of melanoregulators, liporegulators, antiseborrhoeic agents, anti-aging agents, anti-UV agents, keratolytic agents, antibacterial agents, antifungal agents, anti-dandruff agents, agents for combating hair loss, hair dyes, hair bleaches, reducing agents for permanent waves, hair conditioners, and nutrients.

25. The composition of claim 24, wherein said fatty or lipophilic substance is selected from the group consisting of D-α-tocopherol DL-α-tocopherol, D-α-tocopherol acetate, DL-α-tocopherol acetate, ascorbyl palmitate, glycerides of vitamin F, vitamin D, vitamin $D_2$, vitamin $D_3$, retinol, retinol esters, β-carotene, D-panthenol, farnesol, farnesyl acetate, oils of jojoba and of blackcurrant rich in essential fatty acids, 5-n-octanoylsalicylic acid, salicylic acid, alkyl esters of α-hydroxy acids, asiaticoside, whole extract of Centella asiatica, β-glycyrrhetinic acid, α-bisabolol, 2-oleoylamino-1,3-octadecane, phytanetriol, sphingomyelin from milk, phospholipids of marine origin which are rich in polyunsaturated essential acids, ethoxyquine, extract of romarin, extract of balm, quercetin, extract of dried microalgae, essential oil of bergamot, octyl methoxycinnamate, butylmethoxydibenzoylmethane, octyl triazone, yellow, brown, black and red iron oxides, titanium oxides which may be provided in micrometric or nanometric form or in coated form, 3,5-di-tert-butyl-4-hydroxybenzylidene-3-camphor, 2-benzotriazole-2-yl-4-methyl-6-[3-[1,3,3,3-tetramethyl-1-[(trimethylsilyl)oxy]disiloxanyl]-2-methylpropyl]phenol, perfluoronated oil, and hyperoxygenated corn oil.

26. The composition of claim 1, wherein the oil/water ratio is not greater than 1.

27. An oil-in-water emulsion which comprises oily globules each coated with a coating of lamellar liquid crystal and dispersed in an aqueous phase, wherein each oil globule is individually coated with a monolamellar or oligolamellar layer of a mixture of at least one lipophilic surface-active agent, at least one hydrophilic surface-active agent and at least one fatty acid, the coated globules have a mean diameter of less than 500 nanometers and the aqueous phase contains a basic agent in a dissolved state, wherein said lipophilic surface-active agent, said hydrophilic surface-active agent, and said fatty acid are present in a combined amount of between 2 and 6% by weight based on the total weight of said composition.

28. The emulsion of claim 27, wherein the oil/water ratio is not greater than 1.

29. A method of treating skin, comprising applying to skin a composition comprising an oil-in-water emulsion comprising oily globules which are each coated with a lamellar liquid crystal coating and are dispersed in an aqueous phase, each oily globule comprising at least one lipophilic compound which is cosmetically or dermatologically active and is individually coated with a monolamellar or oligolamellar layer of a mixture of at last one lipophilic surface-active agent, at least one hydrophilic surface-active agent, and at least one fatty acid, said coated oily globules having a mean diameter of less than 500 nanometers, and said aqueous phase comprising a basic agent in the dissolved state, wherein said lipophilic surface active agent, said hydrophilic surface-active agent, and said fatty acid are present in a combined amount of between 2 and 6% by weight based on the total weight of said composition.

30. A method of treating hair, comprising applying to hair a composition comprising an oil-in-water emulsion comprising oily globules which are each coated with a lamellar liquid crystal coating and are dispersed in a aqueous phase, each oily globule comprising at least one lipophilic compound which is cosmetically or dermatologically active and is individually coated with a monolamellar or oligolamellar layer of a mixture of at least one lipophilic surface-active agent, at least one hydrophilic surface-active agent, and at least one fatty acid, said coated oily globules having a mean diameter of less than 500 nanometers, and said aqueous phase comprising a basic agent in the dissolved state, wherein said lipophilic surface-active agent, said hydrophilic surface-active agent, and said fatty acid are present in a combined amount of between 2 and 6% by weight based on the total weight of said composition.

* * * * *